United States Patent [19]

Contractor

[11] Patent Number: 5,021,588

[45] Date of Patent: Jun. 4, 1991

[54] VAPOR PHASE CATALYTIC OXIDATION OF BUTANE TO MALEIC ANHYDRIDE

[75] Inventor: Rashmikant M. Contractor, Wilmington, Del.

[73] Assignee: E.I. Du Pont de Nemours and Company, Wilmington, Del.

[21] Appl. No.: 236,743

[22] Filed: Aug. 26, 1988

Related U.S. Application Data

[63] Continuation-in-part of Ser. No. 17,181, Feb. 20, 1987, abandoned, which is a continuation-in-part of Ser. No. 692,474, Jan. 18, 1985, Pat. No. 4,668,802.

[51] Int. Cl.$^5$ ............................................. C07D 307/60
[52] U.S. Cl. ..................................... 549/259; 549/260
[58] Field of Search ................................ 549/259, 260

[56] References Cited

U.S. PATENT DOCUMENTS

| | | | |
|---|---|---|---|
| B 330,354 | 1/1975 | Mount et al. | 352/437 |
| 2,526,689 | 10/1950 | Rollman | 260/342 |
| 2,604,479 | 7/1952 | Rollman | 260/342 |
| 3,864,280 | 2/1975 | Schneider | 252/435 |
| 3,899,516 | 8/1975 | Dickason | 260/346 |
| 3,904,652 | 9/1975 | Frank | 260/346 |
| 4,044,027 | 8/1977 | Anderson et al. | 260/346 |
| 4,062,873 | 12/1977 | Harrison | 260/346 |
| 4,064,070 | 12/1977 | Harrison | 252/435 |
| 4,102,914 | 7/1978 | Beuther et al. | 260/465 |
| 4,111,963 | 9/1978 | Mount et al. | 260/346 |
| 4,132,670 | 1/1979 | Katsumoto et al. | 252/437 |
| 4,151,116 | 4/1979 | McDermott | 252/435 |
| 4,187,235 | 2/1980 | Katsumoto et al. | 260/346 |
| 4,222,945 | 9/1980 | Higgins et al. | 260/346 |
| 4,244,878 | 1/1981 | McDermott | 260/346 |
| 4,261,899 | 4/1981 | Gelbein | 260/346 |
| 4,317,777 | 3/1982 | Higgins et al. | 260/346 |
| 4,317,778 | 3/1982 | Blun et al. | 260/346 |
| 4,342,699 | 8/1982 | Palmer et al. | 549/259 |
| 4,352,755 | 10/1982 | Higgins et al. | 549/258 |
| 4,371,702 | 2/1983 | Bither, Jr. | 549/260 |

FOREIGN PATENT DOCUMENTS 0034442 8/1981 European Pat. Off.

OTHER PUBLICATIONS

Zazhigalov et al., React. Catal. Lett. 24, 375–378 (1984).
C. N. Satterfield, Heterogeneous Catalysis in Practice, McGraw-Hill Book Company 1980, p. 186.
D. J. Hucknall, Selective Oxidation of Hydrocarbons, Academic Press, 1974, pp. 36–37.
Hodnett et al., Ind. Eng. Chem. Fundam. 23, pp. 465–470 (1984).
Cullis, Ind. & Eng. Chem. 59(12) pp. 18–27 (1967).

*Primary Examiner*—Mary C. Lee
*Assistant Examiner*—Bernard I. Dentz

[57] ABSTRACT

The oxidation of butane to maleic anhydride in a recirculating solids reactor using a stoichiometric excess of oxygen, a vanadium-phosphorus oxide catalyst in oxidized form, and separate regeneration of the resultant reduced catalyst is disclosed.

5 Claims, 4 Drawing Sheets

VAPOR PHASE CATALYTIC OXIDATION OF BUTANE TO MALEIC ANHYDRIDE

BACKGROUND OF THE INVENTION

1. Field of the Invention

This invention relates to an improved vapor phase oxidation process for the preparation of maleic anhydride from n-butane over a catalyst containing mixed oxides of vanadium and phosphorus.

2. Background

An important route to maleic anhydride is the vapor phase oxidation of n-butane over a vanadium/phosphorus oxide catalyst. The reaction step involves oxidation of n-butane with air (oxygen) to form maleic anhydride, carbon oxides, water and smaller amounts of partially oxidized by-products. Typically, the process is carried out in multitubular fixed bed reactors. The large exothermal heat and the thermal sensitivity of the n-butane oxidation requires low feed concentrations, expensive heat-transfer equipment, handling of a large volume of gas, and good reactor temperature control. Low butane concentration is also required to avoid flammability conditions. The magnitude of some of these problems is reduced when a fluidized bed reactor is used. The temperature can be readily controlled within a few degrees because of the intensive catalyst mixing and good heat transfer characteristics. Higher butane concentrations can be used because the danger of flammability is greatly reduced by introducing the n-butane directly into the reactor rather than premixing it with air (oxygen). However, very high butane concentrations and low oxygen-to-butane ratios in the reactor may result in over reduction of the catalyst and reduced selectivity to maleic anhydride. Also, significant back-mixing of gases in the fluidized bed reactor encourages maleic anhydride oxidation reactions which reduce selectivity. In addition, rapidly rising gas bubbles in a fluidized bed reactor result in poorer contact between gases in the bubbles and the catalyst, making it difficult to achieve high butane conversion.

A recirculating solids reactor has two reaction zones, in which two separate reactions take place, and a catalyst (the solid) which circulates between the two reaction zones and takes part in both reactions. Such reactor systems have found use in catalytic cracking in petroleum refining and in other reactions. U.S. Pat. No. 4,102,914 discloses a process for the preparation of acrylonitrile by passing a gaseous mixture comprising propylene, ammonia and molecular oxygen and an ammoxidation catalyst through a reaction zone while controlling the superficial linear gas velocity and solids feeds rate to achieve a state of fast fluidization. In a preferred embodiment the lower part of the reactor serves as a regeneration zone and recycled catalyst from the separator is contacted with molecular oxygen prior to the addition of ammonia and propylene. U.S. Pat. No. 4,261,899 discloses a process for preparing phthalic anhydride by oxidizing o-xylene with air (oxygen) in a dilute phase transported bed reactor. Substantially all of the o-xylene is introduced at one end of the reactor while oxygen necessary for the reaction and fluidized catalyst are introduced at a plurality of spaced inlets along the reactor. The catalyst is separated from the product gases and recycled. European Patent Office Publication No. 0 034 442 discloses a process for preparing unsaturated aldehydes (or unsaturated acids) by passing an unsaturated olefin (or unsaturated aldehyde) and oxygen into a transport line reactor with a solid oxidation catalyst to achieve substantially plug flow within the reactor. Reaction products are stripped from the catalyst with steam in the stripper chamber.

The preparation of mixed oxide compositions of vanadium and phosphorus and the use of these as catalysts for the oxidation of hydrocarbons to maleic anhydride is known in the art. In U.S. Pat. No. B330,354 and U.S. Pat. No. 4,111,963 the importance of reducing the vanadium used in a vanadium/phosphorus/ oxygen (V/P/0) catalyst to the +4 oxidation state is described. Preferred is the use of concentrated hydrochloric acid as the reaction medium to bring about this reduction and preferred catalysts have a phosphorus to vanadium atom ratio of 1:2 to 2:1 and a porosity of at least 35%. In U.S. Pat. No. 3,864,280 the reduction of the vanadium in such a catalyst system to an average valence state of 3.9 to 4.6 is emphasized; the atomic ratio of phosphorus to vanadium is 0.9 to 1.8:1. Isobutyl alcohol is used as a solvent for the catalyst preparation, with the indication that an increase in catalyst surface area, over that obtained from use of an aqueous system, is achieved. The addition of promoters to the vanadium/phosphorus oxide catalyst compositions used for the oxidation of hydrocarbons to maleic anhydride is also disclosed in the art. Thus, in U.S. Pat. No. 4,062,873 and U.S. Pat. No. 4,064,070 are disclosed vanadium/phosphorus/silicon catalyst compositions made in an organic medium. In U.S. Pat. No. 4,132,670 and U.S. Pat. No. 4,187,235 are disclosed processes for preparing high surface area vanadium/phosphorus oxide catalysts. Anhydrous alcohols of 1–10 carbon atoms and 1–3 hydroxyl groups are used to reduce the vanadium to a valence of 4.0 to 4.6. Also disclosed are such catalysts containing up to 0.2 mol, per mol of vanadium, of a transition, alkali or alkaline earth metal, for example, tantalum, titanium, niobium, antimony, bismuth or chromium. In U.S. Pat. No. 4,371,702 is disclosed an improved vanadium/phosphorus oxide catalyst containing the promoter comprising silicon and at least one of indium, antimony and tantalum. Zazhigalov et al., React Catal Lett. 24(3-4), 375 (1984), report on microcatalytic studies of the catalytic oxidation of butane over a V/P/0 catalyst and have concluded that maleic anhydride forms mainly due to the gas phase oxygen. They state that on this catalyst the rate of maleic anhydride formation and the process selectivity in the presence of gas phase oxygen is significantly higher than in its absence and that, therefore, only a small part of the maleic anhydride can form at the expense of the catalyst oxygen. C. N. Satterfield, Heterogeneous Catalysis in Practice, McGraw-Hill Book Company, 1980, page 186, discloses that vanadium and other metal oxides capable of rapid and reversible oxidationreduction may be used as an oxygen carrier to cause a partial oxidation reaction, with the carrier being reoxidized in a separate reactor. D. J. Hucknall, Selective Oxidation of Hydrocarbons, Academic Press, 1974, page 36, discloses that selective alkene oxidation over a bismuth molybdate catalyst may be carried out either in the presence or absence of gaseous oxygen.

The following U.S. patents are relevant with respect to a process for the vapor phase oxidation of n-butane to maleic anhydride over a vanadium/ phosphorus oxide catalyst, wherein such process the ratio of n-butane to oxygen is greater than the most commonly employed ratio of about 1:10 and the less commonly employed ratio of 1:4. However, in all of these patents the disclosed procedures require more oxygen in the feed gas than the stoichiometric amount required to convert the total amount of n-butane converted in the process to maleic anhydride. None discloses isolating the reduced catalyst and reoxidizing it before contacting it again with n-butane, none discloses operating with the feed gas substantially free of oxygen, and none discloses operating with the feed gas substantially free of oxygen and the reoxidized catalyst being stripped of oxygen before being contacted again with n-butane.

U.S Pat. No. 3,899,516 discloses an improved process wherein the oxidant is substantially pure oxygen, rather than oxygen diluted with inert gases, for example, with nitrogen, as in air, and the ratio of butane to oxygen is greater than 1:4. Preferably, the ratio is in the range of about 1:1 to 20:1. Mole ratios of 1.6:1 and 3:1 are exemplified but the conversions are 2.2% or less and 1.14%, respectively, so that the amount of oxygen present is more than 8 times the stoichiometric amount required to convert the total amount of n-butane converted in the process.

U.S. Pat. No. 3,904,652 discloses an improved process comprising maintaining, in the reaction zone, an n-butane concentration above 1.7% of the feed, an oxygen concentration of 3–13%, and an inert gas concentration of 70–95%; converting from 30 to 70% of the n-butane; withdrawing a reactor effluent; separating the maleic anhydride; and recycling a major portion of the remaining reactor effluent to the reaction zone. In the five runs disclosed in the example, the amount of oxygen present is at least twice the stoichiometric amount required to convert the total amount of n-butane converted in the process.

U.S. Pat. No. 4,044,027 discloses, in an example, a process wherein the feed gas stream contains 9.1% oxygen and 6.2% butane; however, only 25% of the n-butane is converted.

U.S Pat. Nos. 4,151,116 and 4,244,878 disclose the use of a V/P/0 catalyst having a promoter which is post-deposited upon its surface. The patents further disclose that, typically, the oxidation of butane to maleic anhydride is carried out by means of air or other molecular oxygen-containing gases such as mixtures of carbon dioxide and oxygen or mixtures of nitrogen or steam with air or oxygen, that air is preferred, and that preferably the concentration of butane in the feed will be 1.0 to 1.6 volume % with the oxygen above 10 volume %, and 1.5 to 5 volume % with the oxygen below 0.1 volume %. The examples disclose only the use of a mixture of 1.5 volume % of n-butane in air.

U.S. Pat. No. 4,222,945 discloses a process for oxidizing 10 to 50% of a linear $C_4$ hydrocarbon by contacting it with oxygen. In the process the hydrocarbon concentration is at least 10 molar % and is higher than the explosive limit, the oxygen concentration is greater than 13 molar % of the total material fed to the reaction, and the concentration of any inert gas present is less than 70 molar % of the total material fed to the reaction. The preferred oxygen concentration is 14 to 30 molar %. In all of the examples, the amount of oxygen present is in excess of the stoichiometric amount required to convert the total amount of n-butane converted to maleic anhydride in the process. U.S. Pat. No. 4,317,777 discloses a process for oxidizing 10 to 50% of a hydrocarbon which comprises at least four linear carbon atoms by contacting it with oxygen, the hydrocarbon concentration being greater than 10 molar % and being higher than the explosive limit, the oxygen concentration being greater than 13 molar %, and the concentration of inert gas being greater than 70 molar % of the total material fed to the reaction. The preferred oxygen concentration is 14 to 20 molar %. In the examples, the amount of oxygen present is in excess of the stoichiometric amount required to convert the total amount of n-butane converted to maleic anhydride in the process.

U.S. Pat. No. 4,342,699 discloses a process comprising contacting a non-flammable, n-butane-rich feed consisting essentially of about 2 to about 8 mole % n-butane, about 8 to about 20 mole % molecular oxygen, and a balance of at least one inert gas, and an n-butane oxidation catalyst, in a heat transfer medium-cooled, tubular reaction zone maintained under oxidation conditions which are such as to yield a relatively low per pass conversion of n-butane, the catalyst being graded along at least a portion of the effective length of the reaction zone so as to provide minimum reactivity nearest the feed end of the reaction zone and maximum reactivity nearest the exit end of the reaction zone, and recycling a portion of the effluent with addition of make-up gases comprising n-butane and oxygen.

In all of the examples, the amount of oxygen present is in excess of the stoichiometric amount required to convert the total amount of n-butane converted to maleic anhdyride in the process.

U.S. Pat. No. 4,352,755 discloses a process for producing a gas stream containing at least 2.5% by volume maleic anhdyride by oxidizing a straight chain $C_4$ hydrocarbon with oxygen. The feed stream comprises: the $C_4$ hydrocarbon (25% to 60%, preferably 40 to 55%, and more preferably 45 to 50% by volume); oxygen (20 to 45%, preferably 25 to 35% by volume); and, optionally, inert gases (0 to 30%, preferably 5 to 25%, and more preferably 12 to 20% by volume).

An object of this invention is to provide an improved vapor phase oxidation process for the preparation of maleic anhydride from n-butane over a catalyst containing mixed oxides of vanadium and phosphorus. A further object is to provide a vapor phase oxidation process for the preparation of maleic anhydride from n-butane over a catalyst containing mixed oxides of vanadium and phosphorus, which process is carried out in a recirculating solids reactor. Recirculating solids, transported bed and riser reactors are well known in the art, as is evident from Kahney et al., 66th Annual Meeting, American Institute of Chemical Engineers, Philadephia, Pa., November, 1973; U.S. Pat. No. 3,799,868; and Robertson et al., Chemical Science, 36, 471 (1981). Other objects will become apparent hereinafter.

DETAILED DESCRIPTION OF THE INVENTION

The invention herein resides in an improved process for the selective vapor phase oxidation of n-butane to maleic anhydride using an effective amount of a vanadium/phosphorus oxide catalyst, in oxidized form, the improvement consisting of limiting the amount of oxygen in the feed gas so that it is less than the stoichiometric amount required for the total amount of n-butane converted in the process, the reduced catalyst resulting from the oxidation being separated from the product stream and reoxidized before being contacted again with n-butane. The stoichiometric amount of oxygen required for the total amount of n-butane converted in the process is the amount of oxygen required to convert n-butane to maleic anhydride, that is, 3.5 moles of oxygen for each mole of n-butane converted. Preferably, the amount of oxygen in the feed gas is less than about 30% of the stoichiometric amount, that is, less than about one mole of oxygen for each mole of n-butane converted. In view of the extensive art on butane oxidation processes, the total amount of n-butane converted for a given set of operating conditions can usually be estimated reasonably accurately and, using such conversion data, the less than stoichiometric amount of oxygen to be included in the feed can be calculated. If there is any question about the total amount of n-butane converted, the process can be run under the desired operating conditions, the total amount of n-butane converted can be measured, and the amount of oxygen in the feed can be adjusted to the less than stoichiometric amount, if necessary. If the process of the invention is carried out in a batchwise fashion, the n-butane oxidation can be halted, and the reduced catalyst can be regenerated in place. It is preferred to carry out the process in a recirculating solids reactor wherein the oxidation of the n-butane is carried out in a reaction zone and a substantial part of the oxidation of the resultant reduced catalyst is carried out in a separate regeneration zone.

To increase the selectivity of n-butane to maleic anhydride, it is preferred to carry out the process of the invention so that the feed gas is substantially free of oxygen, provided the catalyst is not overly reduced in the process. It is especially preferred to carry out the process not only so that the feed gas is substantially free of oxygen but also so that the oxidized (regenerated) catalyst is stripped of gas phase oxygen before being contacted again with n-butane. This stripping minimizes the amount of gas phase oxygen which may be present when the oxidized catalyst is contacted with the n-butane. In either preferred embodiment, it is especially preferred to carry out the process in a recirculating solids reactor wherein the oxidation of the n-butane is carried out in a reaction zone and the oxidation of the resultant reduced catalyst is carried out in a separate regeneration zone.

The invention herein also resides in an improved process for the selective vapor phase oxidation of n-butane to maleic anhydride over a vanadium/phosphorus oxide catalyst, in oxidized form, the improvement consisting of carrying out the process in a recirculating solids reactor. More specifically, such process comprises:

a) contacting a feed gas containing n-butane, oxygen and inert gas, where the amount of oxygen present in the feed gas is in excess of the stoichiometric amount required to convert the total amount of n-butane converted to maleic anhydride in the process, with an effective amount of vanadium/phosphorus oxide catalyst, in oxidized form/ comprised of particles about 20 to about 300 $\mu$m in size, in the reaction zone of a recirculating solids reactor, at a temperature of about 300° C. to about 500° C., at a gas residence time in the reaction zone of about 0.5 second to about 15 seconds, and at a catalyst residence time in the reaction zone of about 2 seconds to about 5 minutes;

b) removing the effluent produced in step (a) from the reaction zone and separating the resultant reduced catalyst from the effluent gases, preferably stripping off any effluent gases from the reduced catalyst, transporting the reduced catalyst to the regeneration zone of the recirculating solids reactor, and recovering maleic anhydride from the effluent gases;

c) oxidizing the reduced catalyst in the regeneration zone using an oxygen-containing gas, at a temperature of about 300° C. to about 500° C., at a catalyst residence time in the regeneration zone of about 5 seconds to about 5 minutes, and at an oxygen-containing gas residence time of about 1 second to about 30 seconds; and d) recycling the oxidized catalyst from step (c) to the reaction zone.

The invention herein provides significantly higher conversion of n-butane and higher selectivity to, and yield of, maleic anhydride than can be obtained with known processes using conventional reactors. It also provides a highly concentrated product stream, in a reduced total gas flow, for a desired maleic anhydride production rate. Another advantage of the invention is that good selectivities and conversions can be achieved at lower temperatures than with conventional known processes.

In conventional fixed or fluidized bed reactors, representative of the art, both the oxidation of n-butane over the vanadium/phosphorus oxide catalyst and the regeneration (oxidation) of the reduced vanadium/phosphorus oxide catalyst are carried out in the same reaction zone. Under steady-state conditions the rates of these two oxidation steps must be equal. In order to ensure this equality, sufficient gas phase oxygen must be provided. This may result in reduced selectivity to maleic anhydride and excessive dilution of the product stream.

In the preferred embodiment employing a recirculating solids reactor, the oxidation of n-butane by the vanadium/phosphorus oxide catalyst, in oxidized form, and the reoxidation of the resultant reduced vanadium/phosphorus oxide catalyst by gas phase oxygen are carried out in separate zones, with the conditions for each zone chosen to optimize the step being carried out in that zone without any restrictions imposed by the demands of the other step. Some reoxidation of the catalyst may be carried out in the reaction zone in addition to that carried out in the regeneration zone, if desired, by introducing some gas phase oxygen into the reaction zone. As already stated above, if the process is carried out in a batchwise fashion, the butane oxidation can be interrupted, and the reduced catalyst can be regenerated in place.

In a further description of the embodiment wherein the oxidation of n-butane is carried out in the reaction zone of a recirculating solids reactor, the feed gas is comprised of a mixture of n-butane, oxygen and inert gas. Some of the n-butane used in the feed may be provided by the unconverted n-butane which is present in recycled reaction gas. In some instances, n-butane may be available as the predominant component in a mixture of gases including other hydrocarbons. As long as none of the other gases present significantly adversely affects the process, it may be more convenient to use this n-butane-rich mixture in the feed gas as the source of n-butane. Air can be used as the source of oxygen. The remainder of the feed, to 100 mol %, can be any inert gas, such as nitrogen or recycled reaction gas containing mostly carbon monoxide and carbon dioxide, and possibly unconverted n-butane. Oxidized vanadium/phosphorus oxide catalyst is introduced into the reaction zone. The vanadium/phosphorus oxide particles are about 20 to about 300 $\mu$m in size. The oxidation is carried out at a temperature of about 300° C. to about 500° C., preferably about 340° C. to about 450° C. The reactor exit gas pressure is typically 0–50 psig. The gas residence time in the reaction zone is about 0.5 second to about 15 seconds, and the catalyst residence time is about 2 seconds to about 5 minutes. When there is more than the stoichiometric amount of oxygen in the feed gas, gas residence time in the reaction zone is preferably at least 1.2 seconds, more preferably 1.8 seconds, in order to achieve sufficient conversion to make the process a practical one, that is, to achieve yields of maleic anhydride in a single pass through the reaction zone of at least about 30% and thereby avoid the recycling of excessively large amounts of n-butane. The upper limit of catalyst residence time will, of course, depend on the activity of the catalyst. If still active the catalyst can be retained in the reaction zone for longer than 5 minutes.

The catalyst in the reactor effluent is separated from the effluent gases, and the maleic anhydride product is recovered from the effluent gases, both separations employing conventional techniques and equipment. The separated catalyst is referred to herein as the reduced catalyst because it is in a lower oxidation state than that of the fresh catalyst which enters the reaction zone. When appropriate to the embodiment, the reduced catalyst is preferably stripped of any reactor gases and then recycled to the regeneration zone. The stripped reactor gases are mixed with the reactor effluent gases. After maleic anhydride is recovered from the effluent gases of the reaction zone, the remaining gases may be vented or recycled to the reaction zone. Any off-gases or gas from the regeneration zone can be vented after heat recovery.

The reduced vanadium/phosphorus oxide catalyst is reoxidized in the regeneration zone using an oxygen-containing gas, such as air. The regeneration zone temperature is maintained at about 300° C. to about 500° C., the catalyst residence time in the regeneration zone is about 5 seconds to, typically, about 5 minutes, and the oxygen-containing gas residence time is about 1 to about 30 seconds. Total gas flow rate and oxygen concentration must be sufficient to provide the needed oxygen for catalyst reoxidation to occur within the selected gas and catalyst residence time. The oxidized catalyst is then recycled to the reaction zone.

The required amount of catalyst and the required catalyst circulation rate depend on the extent to which the catalyst oxidation reaction is carried out in the regeneration zone, as opposed to the reaction zone, the amount of n-butane to be reacted, the amount of mobile (or reactive) oxygen contained by the catalyst, and the reaction zone process conditions that determine the amount of catalyst oxygen used per pass. When there is more than the stoichiometric amount of oxygen in the feed gas, the catalyst residence time in the reaction zone is preferably greater than the gas residence time in the reaction zone by a factor of at least 1.5. Even larger differences in the catalyst residence times can be used and the catalyst residence time can be an order of magnitude or more longer than the gas residence time. When oxygen concentration in the reaction zone is low, and substantially all of the catalyst oxidation reaction is carried out in the regeneration zone, a high catalyst circulation rate is required. This rate may be reduced, to the extent that the catalyst oxidation reaction is carried out in the reaction zone.

A recirculating solids reactor can be operated continuously to oxidize n-butane without any gas phase oxygen in the reaction zone. Such operation results in higher selectivity to maleic anhydride than can be attained with conventional reactors, provided an adequate catalyst circulation rate is maintained to supply the needed oxidized catalyst. In order to minimize the gas phase oxygen in the reaction zone, gas phase oxygen is stripped from the oxidized catalyst before recycling the regenerated catalyst to the reaction zone.

Alternatively, if a recirculating solids reactor is operated to oxidize n-butane under conditions of temperature, oxygen and n-butane partial pressures and residence time in the reaction zone identical to those used in conventional reactors, i.e., with the amount of oxygen present in the feed gas in excess of the stoichiometric amount required to convert the total amount of n-butane converted to maleic anhydride in the process, significantly higher conversion of n-butane and significantly higher yield of maleic anhydride are obtained.

The high selectivity to maleic anhydride attained in the recirculating solids reactor is maintained even if the feed to the reaction zone has a very high butane concentration.

Recirculating solids reactors can have many different reactor/regenerator configurations. For example, the reaction zone of the reactor can be comprised of a riser reactor, a fluidized bed reactor, a moving bed reactor, or a combination of both a fluidized bed reactor and a riser reactor. Similarly, the regeneration zone of the regenerator can be comprised of a riser reactor, a fluidized bed reactor, or a combination of both a riser reactor and a fluidized bed reactor. It is to be understood that the invention is not limited to the specific combinations of reactors recited above. A riser or transport line reactor is characterized by high gas velocities of from about 5 ft/s (about 1.5 m/s) to greater than 40 ft/s (12 m/s). Typically, the reactor line is vertically mounted with gas and solids flowing upward in essentially plug flow. The flow can also be downward and the reactor line can be mounted other than vertically. With upward flow of gas and solids, there can be a significant amount of local backmixing of solids, especially at the lower end of the velocity range. The solids concentration in the reaction zone of the reactor can range from, typically, about 1 lb/ft$^3$ (16 kg/m$^3$) to, typically, about 10 lb/ft$^3$ (160 kg/m$^3$), depending on the gas velocity, catalyst particle size and density, and the catalyst circulation rate. A fluidized bed reactor is characterized by extensive solids backmixing and considerable gas backmixing. The gas velocity ranges from about a few inches per second (5–10 cm/s) to about 3 ft/s (about 1 m/s), and the solids concentration ranges from about 20 lb/ft$^3$ to about 45 lb/ft$^3$ (about 300 kg/m$^3$ to about 700 kg/m$^3$) for the vanadium/phosphorus oxide catalyst used in this invention process, the catalyst having a bulk density of about 50 lb/ft$^3$ (about 800 kg/m$^3$). The lower gas velocity and the larger fluidized bed volume makes the fluidized bed a preferred location to install heat exchangers to remove heat and control temperature. The preferred selection of the reactor and the regenerator configurations depends on the activity of the catalyst, the attrition resistance of the catalyst, the relative rate of catalytic degradation of maleic anhydride compared to the production of maleic anhydride, the amount of gas phase oxygen used in the reactor zone, the need for large fluidized bed volume to accommodate heat exchangers, and the impact of these elements on the overall economics.

Figure 1:
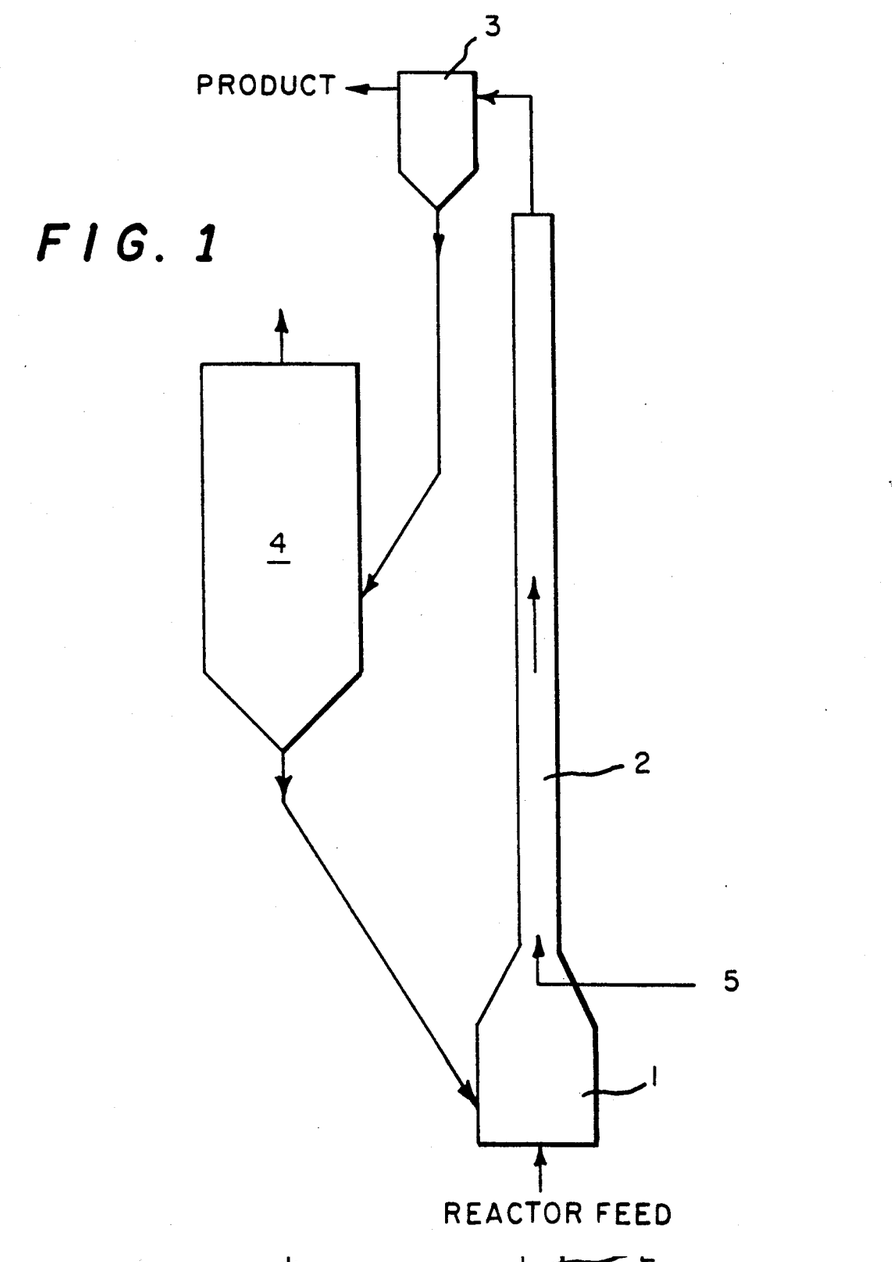
FIG. 1 shows a schematic drawing of a recirculating solids reactor configuration in which the reaction zone is comprised of two parts, a fluid bed section and a riser section, and the regeneration zone is comprised of a fluid bed section.

FIG. 1 is a schematic drawing of one of the recirculating solids reactors used in the examples. The reaction zone is comprised of a fluidized bed section 1 and a riser section 2. The feed gas enters 1 and the oxidation of n-butane takes place in sections 1 and 2. The separator-stripper unit 3 separates and strips off the reaction zone effluent gases from the reduced catalyst. The maleic anhydride product is recovered from the reactor effluent gases leaving 3. The reduced catalyst is transported to the regeneration zone which is comprised of the fluidized bed section 4. The reduced catalyst is oxidized in section 4 and the oxidized (regenerated) catalyst is then recycled to the fluidized bed section 1. The alternate/additional feed line 5 can be used to feed additional oxygen to riser section 2. The recirculating solids reactor of this embodiment can also be operated with just the riser section 2 as the reaction zone. In this mode of operation the feed can be introduced into the riser section 2 through feed line 5.

Figure 2:
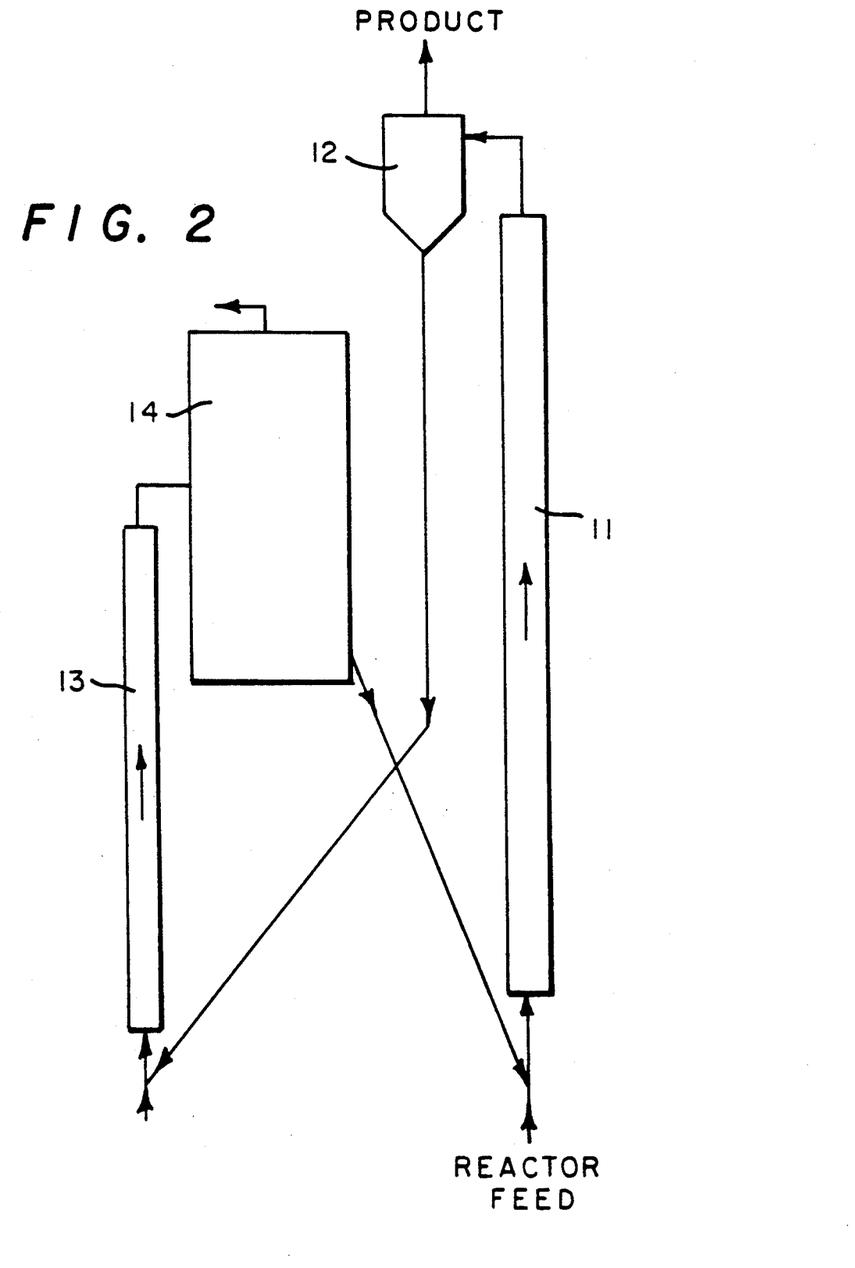
FIG. 2 shows a schematic drawing of a recirculating solids reactor configuration in which the reaction zone is comprised of a riser section and the regeneration zone is comprised of two parts, a riser section and a fluid bed section.

FIG. 2 is a schematic drawing of another recirculating solids reactor used in the examples. The reaction zone is comprised of a riser section 11. The feed gas enters 11 and the oxidation of n-butane takes place in 11. The separator-stripper unit 12 separates and strips off the reaction zone effluent gases from the reduced catalyst. The maleic anhydride product is recovered from the reactor effluent gases leaving 12. The reduced catalyst is transported to the regeneration zone which is comprised of a riser section 13 and a fluidized bed section 14. The reduced catalyst is oxidized in this regeneration zone and the oxidized (regenerated) catalyst is then recycled to the riser section 11.

Figure 3:
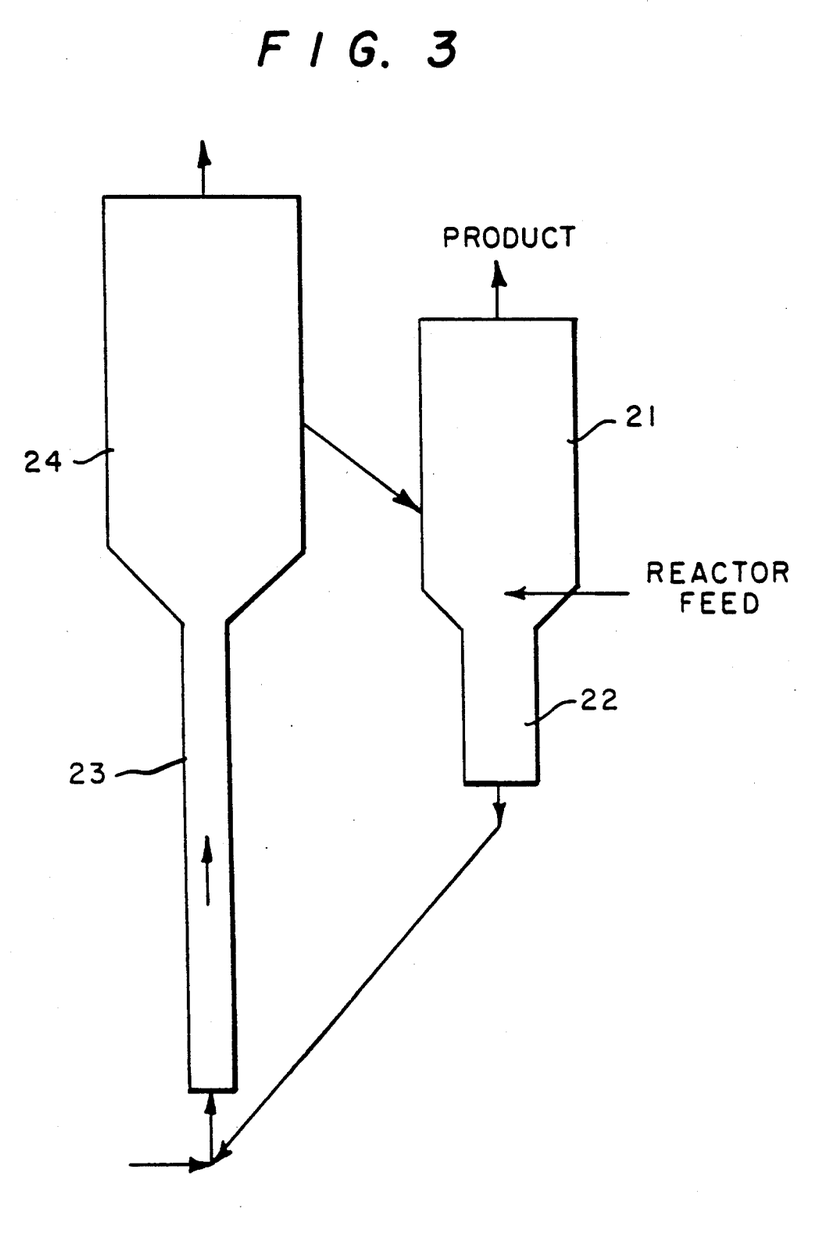
FIG. 3 shows a schematic drawing of a recirculating solids reactor configuration in which the reaction zone is comprised of a fluid bed section and the regeneration zone is comprised of two parts, a riser section and a fluid bed section.

FIG. 3 is a schematic drawing of another recirculating solids reactor used in the examples. The reaction zone is comprised of a fluidized bed section 21. The feed gas enters 21 and the oxidation of n-butane takes place in 21. The stripper unit 22 strips off the reaction zone gases from the reduced catalyst before the reduced catalyst is transported to the regeneration zone The maleic anhydride product is recovered from the reactor effluent. The reduced catalyst is transported to the regeneration zone which is comprised of a riser section 23 and a fluidized bed section 24, where it is oxidized. The oxidized (regenerated) catalyst is then recycled to the fluidized bed section 21.

The reaction and regeneration zones can be within a single reactor, although better process control usually is achieved if the two are in separate units.

The conversion of n-butane in percent is defined as 100 times the number of mols of n-butane converted, divided by the number of mols of n-butane in the feed. The selectivity to maleic anhydride in percent is defined as 100 times the number of mols of n-butane converted to maleic anhydride divided by the total number of mols of n-butane converted. The yield of maleic anhydride in percent is defined as 100 times the number of moles of maleic anhydride formed divided by the number of mols of n-butane in the feed.

As indicated in the Background section of this specification, a number of V/P/0 catalyst preparations and V/P/0 promoters are known in the art. The process of this invention is not limited to a particular method of making the catalyst, nor to a particular promoter.

The catalysts used in the examples of this invention were prepared by substantially following the procedures disclosed in U.S. Pat. No. 4,371,702, particularly the procedures of Examples 1 and 2 thereof. The use of the expression "substantially following the procedures" is not intended as an implication that the same catalyst ingredients were employed, but rather that the same general techniques were used. The following general discussion of the catalyst is excerpted from this patent.

The vanadium/phosphorus oxide (V/P/0) catalyst is made by a process wherein a conventional vanadium compound wherein the vanadium is in the +5 oxidation state, such as in $V_2O_5$ or $NH_4VO_3$, is initially reduced to a substantial degree to the +4 oxidation state by reaction in either an aqueous or organic liquid medium. In an aqueous medium, the reductant can comprise a soluble inorganic compound, such as a halide acid, for example, concentrated hydrochloric acid; a reduced acid of phosphorus, for example, $H_3PO_3$; or a soluble organic compound, for example, formaldehyde, ethylene glycol, or glycolic, oxalic, citric or tartaric acid. In an organic medium, the preferred medium, the reductant can comprise an alcohol(s) selected from such species as n-propyl, isopropyl, n-butyl, isobutyl, and benzyl alcohols. The reduction can be brought about by slurrying the pentavalent vanadium compound in the liquid medium, followed by heating under reflux for the necessary time to bring about reduction.

Preferably, the V/P/0 catalyst includes a promoter which is a combination of selected materials, preferably introduced in both a specific order and chemical form, following the reduction step in which the tetravalent vanadium species is formed. The promoter comprises silicon and at least one of the variable valent elements selected from indium, antimony, and tantalum. In such a catalyst the Si/V atom ratio is in the range 0.02–3.0:1.0, and the (In+Sb+Ta)/V atom ratio is in the range 0.005–0.2:1.0, preferably 0.02–0.12:1.0. The P/V atom ratio is in the range 0.9–1.3:1.0.

In the aqueous system for preparing the catalyst the silicon can be introduced in the form of a colloidal silica sol, for example, as one of the Ludoxl colloidal silica compositions commercially available from E. I. du Pont de Nemours and Company. In the organic system, for example, an alcoholic system, the silicon can be added as an alkyl orthosilicate, for example, tetraethyl orthosilicate. When using an orthosilicate and $V_2O_5$ it is preferable to add at least 0.25 mol of orthosilicate per mol of $V_2O_5$ following substantial reduction of the +5 vanadium to the +4 vanadium species.

Although not necessary to the basic performance of such a V/P/0 catalyst, it is preferred that the indium, antimony and/or tantalum be introduced into the reaction medium as soluble species. Thus, in the organic system, they can be added as a cation with an appropriate attendant anion, for example, an acetate, alkoxide, or anhydrous halide. Although the addition of the indium, antimony and/or tantalum compound can be carried out during the reduction of the pentavalent vanadium species, it is preferred that this addition takes place subsequent to the initial charge of silicon compound, for example, an alkyl orthosilicate, in order to preclude and/or minimize hydrolysis thereof to a less desirable oxide species of indium, antimony and/or tantalum prior to the ultimate addition of the requisite phosphorus compound which completes the formation of the catalyst precursor. The hydrolytic formation of and/or the primary addition of indium, antimony and/or tantalum as slurried oxides, although still giving operable catalyst, leads to more polyphase products showing macro segregation of the adducts in the final catalyst, particularly at higher levels of addition.

Following substantial reduction of the +5 vanadium to the tetravalent species and the introduction of the requisite promoter or promoter precursors the catalyst precursor is formed by the addition of any commonly used appropriate phosphorus compound, for example, phosphoric acid, in such amount that the P/V atom ratio in the ultimate catalyst is in the range 0.9–1.3:1.0, with continued heating of the resultant mixture under reflux to give the catalyst precursor composition that can be isolated by filtration, following cooling of the slurry to room temperature. This product is subsequently dried in air at 80°–200° C. It is a crystalline species having an x-ray diffraction pattern (Cu Ka) with the following major peaks:

| d-value, A | Intensity, $I/I_o$ |
|---|---|
| 5.70 | 100 |
| 4.52 | 43 |
| 3.67 | 29 |
| 3.29 | 37 |
| 3.11 | 17 |
| 2.94 | 54 |
| 2.79 | 14 |
| 2.66 | 16 |
| 1.90 | 11 |

This catalyst precursor is then formed into a convenient catalyst shape, for ultimate charge into a reactor, by gently crushing through a 20-mesh sieve (U.S. Sieve Series), blending the resultant powder with 1–3% of a die lubricant and pellet binder, such as graphite or Sterotexr, a hydrogenated cottonseed oil, commercially available from Capital City Products Co., and tableting to either ⅛" or 3/16" (3.2 or 4.8 mm) diameter pellets.

The pelleted catalyst precursor is fired in a controlled manner in order both to generate and activate the catalyst species for use in the vapor phase oxidation of n-butane to maleic anhydride. Typically, unactivated pellets charged into a 1" (2.54 cm) diameter quartz tube in a vertical furnace are heated, first, in a low flow of air (about 1–3 volumes/volume of catalyst/minute) at 375°–400° C. for 1–6 hours, and then, in a more rapid gas flow (about 3–6 volumes/volume of catalyst/minute) of 1–1.5% n-butane in air (by volume) at 450°–490° C. for about 16–24 hours. The resultant pellets are then ready for use in the production of maleic anhydride.

In the following examples all temperatures are in degrees Celsius, residence times are in seconds, gas compositions are in mol percent, conversions and selectivities are in percent, and the gas pressure at the reactor exit was about 1 psig (6.9 kPa).

EXAMPLE 1

A recirculating solids reactor of the type shown in FIG. 1 was used to oxidize n-butane to maleic anhydride. A feed gas consisting of 3 mol % n-butane and 97 mol % nitrogen (that is, free of oxygen) was introduced into the reactor fluidized bed section 1 and contacted with the vanadium/phosphorus oxide catalyst at a temperature of 438°. Before use, the V/P/0 catalyst pellets were crushed and sieved to obtain the desired catalyst particle size, about 75 to about 250 μm. The total gas residence time in the reaction zone was about 4 seconds.

The regeneration zone was maintained at the same temperature and exit pressure as the reaction zone and a gas stream containing 20 mol % oxygen and 80 mol % helium was introduced into it to oxidize the catalyst for recycle. The $O_2$/He gas residence time was 3 seconds.

Maleic anhydride yields were determined by quenching the product stream with water and titrating the recovered maleic anhydride in the quenched water with 0.1N NaOH solution. Product gas stream samples obtained after quenching were analyzed for $O_2$, $N_2$, CO, $CO_2$, unconverted n-butane, and lower hydrocarbons. No such hydrocarbon species were detected in any of the samples. The conversion of n-butane was 83.3% and the selectivity to maleic anhydride was 60.8%. The reaction conditions and the resulting data are summarized in Table I.

The results show that n-butane can be oxidized to maleic anhydride with high selectivity at high conversion in the absence of gas phase oxygen in the reaction zone of the recirculating solids reactor. Oxygen for the reaction is supplied by the recirculating oxidized catalyst; the reduced catalyst is oxidized in a separate regeneration zone.

EXAMPLE 2

Example 1 was repeated, except that the temperature was 376° and the feed gas into the reaction zone contained 2.1% butane, 8.5% oxygen and 89.4% nitrogen. The reaction conditions and resulting data are summarized in Table I.

The experiment of Example 2 was repeated (Comparative Experiment A), except that the feed gas into the regeneration zone was helium. The reaction conditions and resulting data are summarized in Table I.

The results show that the selectivities are substantially the same in Example 2 and showing A (outside the invention), presumably because the reaction temperature and the oxygen partial pressure were nearly identical. However, Example 2 gave considerably higher conversion than Showing A because of the recirculation of oxidized catalyst in Example 2.

TABLE I

| | Reaction Zone | | | | | | Reg'n. Zone | | | |
|---|---|---|---|---|---|---|---|---|---|---|
| | React. & Regen. | Gas Res. | Feed Gas | | | Feed Gas | | Gas Res. | | |
| Ex. No. | Temp. | Time | n-butane | $O_2$ | $N_2$ | $O_2$ | He | Time | Conv. | Sel. |
| 1. | 438 | 4 | 3 | 0 | 97 | 20 | 80 | 3 | 83.3 | 60.8 |

TABLE I-continued

| | Reaction Zone | | | | | | Reg'n. Zone | | | |
|---|---|---|---|---|---|---|---|---|---|---|
| | React. & Regen. | Gas Res. | Feed Gas | | | Feed Gas | | Gas Res. | | |
| Ex. No. | Temp. | Time | n-butane | $O_2$ | $N_2$ | $O_2$ | He | Time | Conv. | Sel. |
| 2. | 376 | 4 | 2.1 | 8.5 | 89.4 | 20 | 80 | 5 | 59.3 | 68.3 |
| A. | 379 | 4 | 2.1 | 8.5 | 89.4 | 0 | 100 | 5 | 48.1 | 67.2 |

EXAMPLES 3-8

Examples 3-8 were carried out using the procedure and a recirculating solids reactor of the type described in Example 1 to oxidize n-butane to maleic anhydride. Comparative Experiments B-G (outside the invention) were carried out using a conventional fluidized bed reactor to oxidize n-butane to maleic anhydride.

The V/P/0 catalyst was formed into pellets which were calcined in air at 390° for 1 hour. The pellets were then crushed and sieved to the desired size. The catalyst used was a mixture of 71 parts, by weight, of a V/P/0 catalyst containing 1% antimony, 1% indium and 2% silicon as promoter and 29 parts, by weight, of a V/P/0 catalyst, of similar particle size, containing 4% tantalum and 2% silicon as promoter. This catalyst mixture was then activated in a fluidized bed reactor using 1.4 mol % n-butane in air at 450° for 24 h. The activated catalyst particle size was about 75 to about 250 μm.

The reaction conditions and resulting data are summarized in Table II. The results show considerably higher selectivities for Examples 3-8 in which the recirculating solids reactor was used with no gas phase oxygen fed to the reaction zone, than for Comparative Experiments B-G in which the fluidized bed reactor was used.

bed reactor in an atmosphere consisting of 1.5 mol % n-butane, 12 mol % oxygen and 86.5 mol % nitrogen.

The procedure used to oxidize n-butane in the conventional fluidized bed reactor was substantially the same as that used for Comparative Experiments B-G. Experiments were carried out at reactor temperatures of 375°, 405°, and 420°. In each instance the gas feed consisted of 1.5 mol % n-butane, 12 mol % oxygen and 86.5 mol % nitrogen. The gas residence time was 7 seconds.

The procedures used to oxidize n-butane in the three recirculating solids reactors were similar to the procedure used in Example 1, except that in some of these experiments the reaction zone consisted of a fluidized bed reaction section, in some the reaction zone consisted of a riser reaction section, and in other experiments the reaction zone consisted of a fluidized bed reaction section and a riser reaction section. Similarly, in some experiments the regeneration zone consisted of only a fluidized bed reaction section, and in other experiments the regeneration zone consisted of a riser reaction section as well as a fluidized bed reaction section. The regeneration zone temperature and pressure in these experiments were the same as the reaction zone temperature and pressure. The regenerator feed gas consisted of 20 mol % oxygen and 80 mol % helium.

TABLE II

| | Reaction Zone | | | | | | Regeneration Zone | | | | | |
|---|---|---|---|---|---|---|---|---|---|---|---|---|
| | | Gas Res. | Feed Gas | | | | Gas Res. | Feed Gas | | | | |
| Ex. No. | Temp. | Time | n-butane | $O_2$ | $N_2$ | Temp. | Time | $O_2$ | He | % Conv. | % Sel. |
| 3 | 357 | 5 | 1.2 | 0 | 98.8 | 355 | 4 | 20 | 80 | 46.6 | 90.1 |
| 4 | 355 | 5 | 11.0 | 0 | 89.0 | 355 | 4 | 20 | 80 | 9.0 | 90.8 |
| 5 | 356 | 5 | 5.4 | 0 | 94.6 | 355 | 4 | 20 | 80 | 16.0 | 83.2 |
| 6 | 350 | 3.2 | 3.5 | 0 | 96.5 | 350 | 4 | 20 | 80 | 16.3 | 93.2 |
| 7 | 363 | 5 | 2.7 | 0 | 97.3 | 360 | 4 | 20 | 80 | 30.2 | 85.7 |
| 8 | 358 | 5 | 1.2 | 0 | 98.8 | 355 | 4 | 20 | 80 | 47.7 | 88.2 |
| B | 356 | 6.4 | 1.3 | 20.7 | 78.0 | n.a. | n.a | n.a. | n.a. | 60.4 | 66.0 |
| C | 363 | 6.4 | 1.0 | 20.8 | 78.2 | n.a. | n.a | n.a. | n.a. | 68.0 | 66.7 |
| D | 357 | 4.7 | 1.0 | 20.8 | 78.2 | n.a. | n.a | n.a. | n.a. | 49.7 | 63.2 |
| E | 369 | 6.4 | 1.3 | 10.0 | 88.7 | n.a. | n.a | n.a. | n.a. | 54.9 | 65.3 |
| F | 355 | 6.4 | 1.3 | 5.0 | 93.7 | n.a. | n.a | n.a. | n.a. | 36.8 | 76.0 |
| G | 354 | 6.4 | 2.8 | 5.0 | 92.2 | n.a. | n.a | n.a. | n.a. | 22.8 | 75.6 | n.a. = not applicable

EXAMPLE 9

Experiments were carried out using three recirculating solids reactors having configurations of the type shown in FIGS. 1, 2 and 3, respectively, and, for comparison, using a conventional fluidized bed reactor. The vanadium/ phosphorus oxide catalyst used in these experiments contained 10 wt % silica (incorporated into the catalyst precursor slurry) to improve attrition resistance of the catalyst. The catalyst, after spray drying, was screened and the particles of size 75 to 250 μm were calcined in air at 390° for 1 h. The calcined catalyst was then activated by heating at 450° for 16 h in a fluidized The gas residence time in the regeneration zone was about 5 seconds for all experiments. The range of operating conditions used in the reaction zone during these experiments were:
mol % n-butane in feed gas: 1.0 to 50.0%
mol % oxygen in feed gas: 0 to 8%
balance of feed gas: nitrogen
gas residence time: 0.7 to 7.0 seconds
temperature: 360° and 420°

Figure 4:
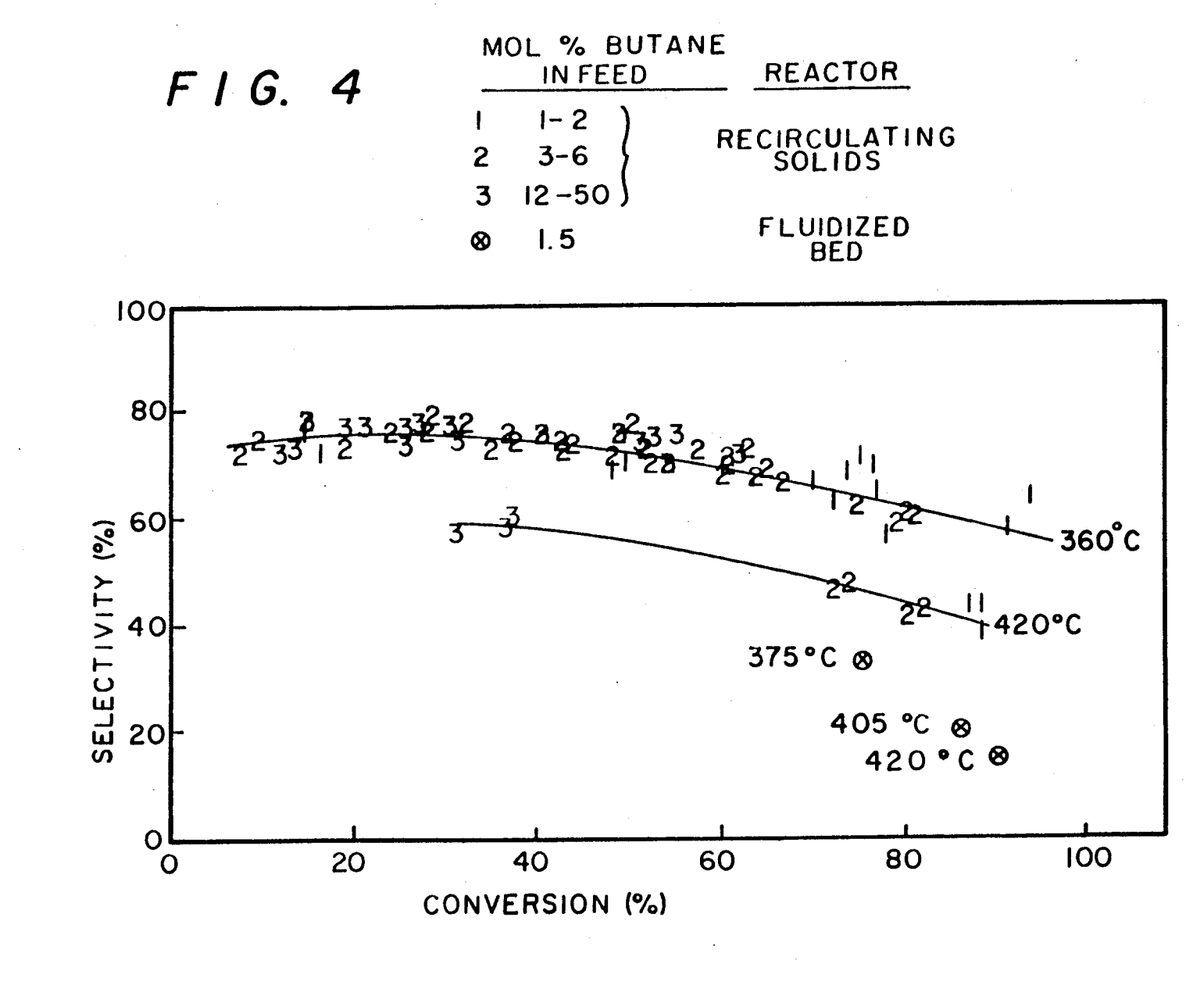
FIG. 4 shows a plot of conversion of n-butane vs. selectivity for Example 8.

FIG. 4 shows the results of these experiments plotted as conversion versus selectivity at two different temperatures used in the recirculating solids reactors. The conversion versus selectivity for the three experiments carried out in the conventional fluidized bed reactor are also shown in FIG. 4.

The results for the recirculating solids reactors show that conversion increases as the amount of n-butane in the feed decreases and increases with increase in: a) the mol % of oxygen in the feed, b) the gas residence time in the reaction zone, and c) the reaction zone temperature. However, at a constant reaction temperature the effect of the mol % n-butane in the feed and the gas residence time in the reaction zone on the conversion versus selectivity relationship was smaller than the scatter in the data. Thus, a change in the mol % of n-butane in the feed over the range 1 to 50% did not affect the selectivity at any constant conversion achieved by adjusting other process variables. Similarly, the use of three different reaction zone configurations, two different regeneration zone configurations, and several different gas residence times did not significantly affect the conversion versus selectivity relationship. About half of these experiments were carried out using no gas phase oxygen in the reaction zone and about half were carried out using 8 mol % oxygen in the feed gas. The experiments carried out with no gas phase oxygen in the reaction zone generally showed somewhat higher selectivities at a given conversion. An increase in reaction temperature resulted in a decrease in selectivity at a given conversion. The selectivities in the experiments carried out in the conventional fluidized bed reactor were significantly lower than those achieved in the recirculating solids reactors.

These results clearly show that the recirculating solids reactor gives significantly higher selectivity to maleic anhydride and higher conversion of n-butane, and it eliminates any restrictions on n-butane concentration in the feed gas.

EXAMPLES 10-11

A recirculating solids reactor of the type described in Example 1 was used to oxidize n-butane to maleic anhydride. The procedure used was substantially the same as that used in Example 1 and the catalyst was the same as that used in Example 9. The two examples were carried out under substantially identical reaction conditions, except that in Example 11 the oxidized catalyst leaving the regeneration zone was stripped of oxygen using helium as a stripping gas. This stripping was done in order to minimize any oxygen gas from the regeneration zone being carried into the reaction zone with the circulating oxidized catalyst. The reaction conditions and the resulting data are summarized in Table III and show that considerably higher selectivity is achieved in Example 11, compared to that of Example 10.

TABLE III

| | Reaction Zone | | | | | | Reg'n Zone | | |
|---|---|---|---|---|---|---|---|---|---|
| | React. & | Gas | | | | | | Gas | | |
| Ex. | Regen. | Res. | Feed Gas | | | Feed Gas | | Res. | | |
| No. | Temp. | Time | n-butane | $O_2$ | $N_2$ | $O_2$ | He | Time | Conv. | Sel. |
| 10 | 360 | 3.5 | 3.0 | 0 | 97.0 | 20.0 | 80.0 | 5 | 51.5 | 69.8 |
| 11 | 360 | 3.5 | 3.0 | 0 | 97.0 | 20.0 | 80.0 | 5 | 49.1 | 77.0 |

EXAMPLES 12-14

A recirculating solids reactor of the type used in Example 1 was used to oxidize n-butane in Examples 12, 13, and 14. The procedure used was substantially the same as that used in Example 1 and the catalyst was the same as that used in Example 9. The three examples were carried out under substantially identical reaction conditions, except that different oxygen concentrations were used in the reaction zone feed gas.

The feed gas compositions for the reaction zone and the regeneration zone, the conditions in the reaction zone and in the regeneration zone, and the results for these examples are given in Table IV. The results show that the selectivity increases as the amount of oxygen in the feed is decreased from 71% of the stoichiometric amount required for the total amount of n-butane converted in Example 12, to 28% of the stoichiometric amount required for the total amount of n-butane converted in Example 13, to 0% of the stoichiometric amount required for the total amount of n-butane converted in Example 14.

TABLE IV

| | Reaction Zone | | | | | | | Reg'n. Zone | | |
|---|---|---|---|---|---|---|---|---|---|---|
| | React. & | Gas | | | | | | | Gas | | |
| Ex. | Regen. | Res. | Feed Gas | | | Feed Gas | | | Res. | | |
| No. | Temp. | Time | n-butane | $O_2$ | $N_2$ | $O_2$ | He | Time | Conv. | Sel. |
| 12 | 360 | 7.4 | 12 | 16 | 72 | 20 | 80 | 5.0 | 53.2 | 69.5 |
| 13 | 360 | 4.6 | 12 | 6 | 82 | 20 | 80 | 5.0 | 51.5 | 74.8 |
| 14 | 360 | 4.6 | 12 | 0 | 88 | 20 | 80 | 5.0 | 47.7 | 75.2 |

EXAMPLE 15

A recirculating solids reactor of the type shown in FIG. 1 was used to oxidize n-butane to maleic anhydride. The procedure employed in the oxidation process was substantially the same as that used in Example 1. The catalyst utilized was made in substantially the same manner as that in Example 9. The regeneration gas was air and the gas residence time in the regeneration zone was about 5 seconds. The reaction zone and the regeneration zone temperatures were between 418° C. and 421° C. during the entire 80 hour run. The feed gas into the reaction zone contained 4.0 mol % commercial grade butane (about 97% n-butane), 8.0 mol % oxygen and the balance nitrogen. Gas residence time in the reaction zone was about 3 seconds.

The average n-butane conversion for the 80 hour run was 50.7%. Thus the amount of oxygen present in the feed gas was in excess of the stoichiometric amount required to convert the total amount of n-butane converted to maleic anhydride in the process by a factor of 1.16, that is, the amount of oxygen present in the feed gas is 116% of the stoichiometric amount. The instantaneous conversion varied somewhat but at all times the amount of oxygen in the feed gas exceeded the stoichiometric amount.

The average selectivity to maleic anhydride obtained using the recirculating solids reactor and oxidizing the reduced catalyst in the regeneration zone was 76.5%. Comparison with the selectivities obtained in runs carried out in a conventional fluidized bed reactor at about the same n-butane conversion, for example, Comparative Experiments D and E, which had selectivities of 63.2% and 65.3%, respectively, shows that when oxygen in the feed gas is in excess of the stoichiometric amount there is a considerable advantage to carrying out the reaction in a recirculating solids reactor and oxidizing the reduced catalyst in the regeneration zone.

EXAMPLES 16-19

A recirculating solids reactor of the type shown in FIG. 1 was used to oxidize n-butane to maleic anhydride. The procedure employed in the oxidation process was substantially the same as that used Example 1 except that the feed gas was introduced through the alternate feed line 5 shown in FIG. 1. The catalyst utilized was the same as that used in Example 15. The reaction zone and the regeneration zone temperatures were 420° C. Oxidation runs were carried out with the feed gas containing wither 2 mol % or 3 mol % n-butane. In both instances, the ratio of oxygen to n-butane in the feed gas was 4 and the remainder of the feed gas was nitrogen. The gas residence time in the reaction zone was 0.6, 0.9 and 1.2 seconds. A gas stream consisting of either 100% air (Examples 16-19) or 100% nitrogen (Comparative Experiments H-K) was passed through the regeneration zone. The gas residence time residences in the regeneration zone was about 5 seconds. The gas residence times in seconds, catalyst residence times in seconds, feed gas and regeneration zone gas compositions and the resulting data are shown in Table V.

The amount of oxygen present in the feed gas was well in excess of the stoichiometric amount required to convert the total amount of n-butane converted to maleic anhydride in the process for all of these Examples and Comparative Experiments. Comparison of the conversions obtained in Comparative Experiments H-K carried out with no oxidation of the reduced catalyst in the regeneration zone shows that there is a considerable advantage to carrying out the reaction in the recirculating solids reactor and oxidizing the reduced catalyst in the regeneration zone.

EXAMPLES 20-21

A recirculating solids reactor of the type shown in FIG. 1 was used to oxidize n-butane to maleic anhydride. The procedure used was substantially the same as that used in Example 1. The catalyst used was the same as that used in Examples 16-19. The reaction zone and the regeneration zone temperatures were 420° C. Oxidation runs were carried out with the feed gas containing 4 mol % n-butane. The gas residence time in the reaction zone was 2.8 seconds and the catalyst residence time in the reaction zone was 20.0 seconds. A gas stream consisting of 100% air was passed through the regeneration zone. The gas residence time in the regeneration zone was about 5 seconds. The gas residence times in seconds, catalyst residence times in seconds, feed gas and regeneration zone gas compositions and the resulting data are shown in Table V.

The amount of oxygen present in the feed gas is well in excess of the stoichiometric amount required to convert the total amount of n-butane converted to maleic anhydride in the process for these Examples.

EXAMPLES 22-24

A recirculating solids reactor of the type shown in Figure was used to oxidize n-butane to maleic anhydride. The procedure used was substantially the same as that used in Example 1 and Examples 20 and 21. The catalyst used ws of the type used in Example 9. The reaction zone and the regeneration zone temperatures were 420° C. Oxidation runs were carried out with the feed gas containing 1.2, 2.2 and 4.4 mol % n-butane. The gas residence time in the reaction zone was 1.8 seconds, and the catalyst residene time in the reaction zone was 6.0 seconds. A gas stream consisting of 100% air was passed through the regeneration zone. The gas residence time in the regeneration zone was about 5 seconds. The gas residence times in seconds, catalyst residence times in seconds, feed gas and regeneration zone gas compositions and the resulting data are shown in Table V.

The amount of oxygen present in the feed gas is well in excess of the stoichiometric amount required to convert the total amount of n-butane converted to maleic anhydride in the process for these Examples.

Comparison of the results for Examples 16-24 show that as the gas residence time in the reaction zone is increased the amount of n-butane converted increases and a gas esidence time of at least about 1.2 seconds is required to give a conversion of at least about 30%. Longer gas residence times result in higher conversions and residence times of 1.8 seconds result in conversions of 50% and higher for typical gas compositions. These Examples also show that the catalyst residence time in the reaction zone is at least 1.5 times the gas residence time in the reaction zone and that the ratio between the two residence times can be increased considerably while maintaining conversion and selectivity. This is preferred since it requires less rapid circulation of the catalyst.

TABLE V

| Ex. No | Reaction Zone | | Feed Gas | | | Reg'n Zone Gas | % Conv. | % Sel. |
|---|---|---|---|---|---|---|---|---|
| | Gas Res. Time | Cat. Res. Time | n-butane | O$_2$ | N$_2$ | | | |
| 16 | 0.6 | 0.9 | 2 | 8 | 90 | Air | 11 | 71 |
| H | 0.6 | 0.9 | 2 | 8 | 90 | N$_2$ | 4 | 66 |
| 17 | 0.9 | 1.4 | 2 | 8 | 90 | Air | 20 | 71 |
| I | 0.9 | 1.4 | 2 | 8 | 90 | N$_2$ | 7 | 70 |
| 18 | 0.9 | 1.4 | 3 | 12 | 85 | Air | 16 | 73 |
| J | 0.9 | 1.4 | 3 | 12 | 85 | N$_2$ | 7 | 70 |
| 19 | 1.2 | 2.0 | 2 | 8 | 90 | Air | 31 | 72 |
| K | 1.2 | 2.0 | 2 | 8 | 90 | N$_2$ | 11 | 71 |
| 20 | 2.8 | 20.0 | 4 | 8 | 88 | Air | 54 | 70 |
| 21 | 2.8 | 20.0 | 4 | 14 | 82 | Air | 55 | 68 |
| 22 | 1.8 | 6.0 | 1.2 | 9 | 89.8 | Air | 86 | 57 |
| 23 | 1.8 | 6.0 | 2.2 | 9 | 88.8 | Air | 74 | 62 |
| 24 | 1.8 | 6.0 | 4.4 | 9 | 86.6 | Air | 54 | 67 |

BEST MODE FOR CARRYING OUT THE INVENTION

The best mode presently contemplated for carrying out the invention is represented by the entire disclosure herein, it being understood that selection of the best mode will depend on a variety of factors, including yield, selectivity and economics.

What is claimed is:

1. Improved process for the selective vapor phase oxidation of n-butane to maleic anhydride over a vanadium/phosphorus oxide catalyst, in oxidized form, the improvement consisting of:
   a) contacting a feed gas containing n-butane, oxygen and inert gas, where the amount of oxygen present in the feed gas is in excess of the stoichiometric amount required to convert the total amount of n-butane converted to maleic anhydride in the process,
   with an effective amount of vanadium/phosphorus oxide catalyst, in oxidized form, comprised of particles about 20 to about 300 μm in size,
   in the reaction zone of a recirculating solids reactor, at a temperature of about 300° C. to about 500° C., at a gas residence time in the reaction zone of about 1.2 seconds to about 15 seconds, and at a catalyst residence time in the reaction zone of at least 1.5 times greater than the gas residence time;
   b) removing the effluent produced in step (a) from the reaction zone and separating the resultant reduced catalyst from the effluent gases, transporting the reduced catalyst to the regeneration zone of the recirculating solids reactor, and recovering maleic anhydride from the effluent gases;
   c) oxidizing the reduced catalyst in the regeneration zone using an oxygen-containing gas, at a temperature of about 300° C. to about 500° C., at a catalyst residence time in the regeneration zone of about 5 seconds to about 5 minutes, and at an oxygen-containing gas residence time of about 1 second to about 30 seconds; and
   d) recycling the oxidized catalyst from step (c) to the reaction zone.

2. Process of claim 1 wherein the gas residence time in the reaction zone is at least about 1.8 seconds to about 15 seconds.

3. Process of claim 1 wherein any effluent gases are stripped off from the reduced catalyst before transporting the reduced catalyst to the regeneration zone of the recirculating solids reactor.

4. Process of claim 1 wherein the reaction zone and the regeneration zone are each comprised of a riser reactor and/or a fluidized bed reactor.

5. Process of claim 3 wherein the reaction zone and the regeneration zone are each comprised of a riser reactor and/or a fluidized bed reactor.

* * * * *